United States Patent
Quan et al.

(10) Patent No.: US 11,045,417 B2
(45) Date of Patent: Jun. 29, 2021

(54) COATING LIQUID FOR MICRONEEDLES, MICRONEEDLE-COATING SUBSTANCE, AND MICRONEEDLE ARRAY

(71) Applicant: COSMED PHARMACEUTICAL CO., LTD., Kyoto (JP)

(72) Inventors: Ying-shu Quan, Kyoto (JP); Mio Saito, Kyoto (JP); Shouta Kitaoka, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 16/075,099

(22) PCT Filed: Feb. 1, 2017

(86) PCT No.: PCT/JP2017/003565
§ 371 (c)(1),
(2) Date: Aug. 2, 2018

(87) PCT Pub. No.: WO2017/135290
PCT Pub. Date: Aug. 10, 2017

(65) Prior Publication Data
US 2019/0038550 A1 Feb. 7, 2019

(30) Foreign Application Priority Data
Feb. 3, 2016 (JP) .............................. JP2016-018844

(51) Int. Cl.
| | | |
|---|---|---|
| *A61K 9/00* | (2006.01) | |
| *A61K 47/10* | (2017.01) | |
| *A61K 47/26* | (2006.01) | |
| *A61K 47/32* | (2006.01) | |
| *A61K 47/34* | (2017.01) | |
| *A61K 47/38* | (2006.01) | |
| *A61K 9/08* | (2006.01) | |
| *A61M 37/00* | (2006.01) | |
| *A61K 39/12* | (2006.01) | |
| *A61K 47/36* | (2006.01) | |

(52) U.S. Cl.
CPC .............. *A61K 9/0021* (2013.01); *A61K 9/08* (2013.01); *A61K 39/12* (2013.01); *A61K 47/10* (2013.01); *A61K 47/26* (2013.01); *A61K 47/32* (2013.01); *A61K 47/34* (2013.01); *A61K 47/36* (2013.01); *A61K 47/38* (2013.01); *A61M 37/00* (2013.01); *A61M 37/0015* (2013.01); *A61M 2037/0023* (2013.01); *A61M 2037/0061* (2013.01)

(58) Field of Classification Search
CPC ........ A61K 47/10; A61K 47/26; A61K 47/34; A61K 9/08; A61K 47/36; A61K 9/70; A61K 47/32; A61K 9/0021; A61K 47/38; A61M 37/0015; A61M 37/00; A61M 2037/0061; A61M 2037/0023
See application file for complete search history.

(56) References Cited

U.S. PATENT DOCUMENTS

| | | | |
|---|---|---|---|
| 6,603,998 B1 | 8/2003 | King et al. | |
| 2002/0061589 A1 | 5/2002 | King et al. | |
| 2002/0193729 A1 | 12/2002 | Cormier et al. | |
| 2004/0203124 A1 | 10/2004 | King et al. | |
| 2006/0040864 A1 | 2/2006 | Ameri et al. | |
| 2006/0074377 A1 | 4/2006 | Cormier et al. | |
| 2009/0143724 A1 | 6/2009 | Cormier et al. | |
| 2010/0280457 A1 | 11/2010 | Tokumoto et al. | |
| 2012/0130306 A1 | 5/2012 | Terahara et al. | |
| 2013/0072874 A1 | 3/2013 | Tokumoto et al. | |
| 2013/0123707 A1* | 5/2013 | Determan | A61K 9/0021 604/173 |
| 2014/0170299 A1* | 6/2014 | Gill | A61M 37/0015 427/2.28 |
| 2015/0216796 A1* | 8/2015 | Ishibashi | A61K 39/00 604/46 |

(Continued)

FOREIGN PATENT DOCUMENTS

| | | |
|---|---|---|
| CN | 102917722 A | 2/2013 |
| EP | 2 578 264 A1 | 4/2013 |

(Continued)

OTHER PUBLICATIONS

International Search Report for the Application No. PCT/JP2017/003565 dated Mar. 7, 2017.
Written Opinion of the International Searching Authority (PCT/ISA/237) for Application No. PCT/JP2017/003565 dated Mar. 7, 2017.
Written Opinion of the International Searching Authority (PCT/ISA/237) for Application No. PCT/JP2017/003565 dated Mar. 7, 2017 (English Translation dated Aug. 16, 2018).

(Continued)

*Primary Examiner* — Doan T Phan
(74) *Attorney, Agent, or Firm* — Cheng Law Group, PLLC

(57) ABSTRACT

To provide a composition of a coating liquid for microneedle which is optimal for coating a microneedle with a medicinal ingredient.

The coating liquid for microneedle of the present invention is an aqueous solution containing, as essential components of a base, a water-soluble polysaccharide, a monosaccharide and/or a disaccharide and a surfactant, characterized in that a ratio of the water-soluble polysaccharide to the base is 2 to 60 mass %, and the hardness after being dried is 10 N or more. The coating liquid for microneedle may further contain a water-soluble polyalcohol, and preferably a monosaccharide and/or a disaccharide is 30 to 95 mass %, a surfactant is 0.05 to 5 mass %, and a water-soluble polyalcohol is 10 mass % or less in the base. As the water-soluble polysaccharide, hydroxypropyl cellulose, hyaluronic acid, or carboxymethyl cellulose is preferable.

5 Claims, 1 Drawing Sheet

(56) References Cited

U.S. PATENT DOCUMENTS

2016/0001053 A1* 1/2016 Quan ............... A61M 37/0015
604/46

FOREIGN PATENT DOCUMENTS

| JP | 2002-535100 A | 10/2002 |
| JP | 2004-535048 A | 12/2004 |
| JP | 2008-510520 A | 4/2008 |
| JP | WO-2008-139648 A1 | 7/2010 |
| JP | 2011-224308 A | 11/2011 |
| JP | WO-2010-143689 A1 | 11/2012 |
| WO | WO-2008/139648 A1 | 11/2008 |
| WO | WO-2011/148994 A1 | 12/2011 |
| WO | WO-2012/115207 A1 | 8/2012 |
| WO | WQ-2014126052 A1 * | 8/2014 ........ A61M 37/0015 |

OTHER PUBLICATIONS

Kim, Yeu-Chun et al., "Improved influenza vaccination in the skin using vaccine coated microneedles", Vaccine, 2009, vol. 27, pp. 6932-6938.

Supplementary European Search Report for the Application No. EP 17 747 446.7 dated Sep. 3, 2019.

European Office Action for the Application No. 17 747 446.7 dated Jul. 6, 2020.

The First Office Action for the Application No. 201780009633.0 from the State Intellectual Property Office of the People's Republic of China dated Dec. 18, 2020.

* cited by examiner

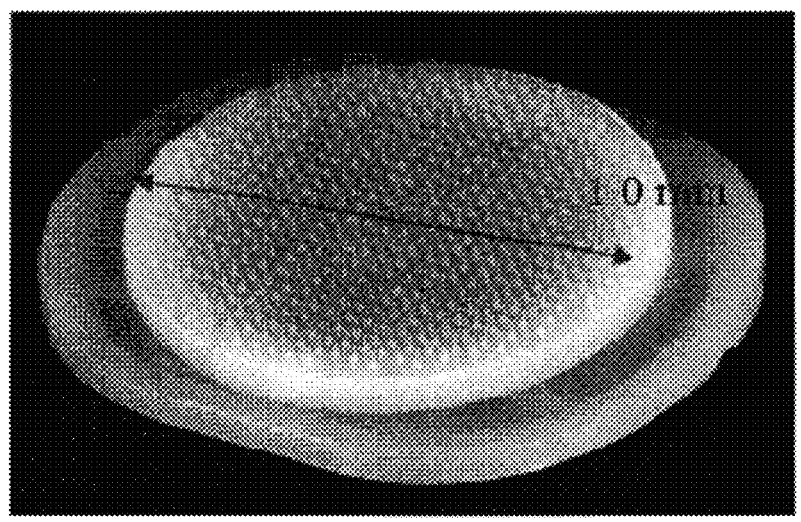

US 11,045,417 B2

COATING LIQUID FOR MICRONEEDLES, MICRONEEDLE-COATING SUBSTANCE, AND MICRONEEDLE ARRAY

TECHNICAL FIELD

The present invention relates to a coating liquid for coating a microneedle with a medicament and a coating material obtained by being dried on a microneedle tip end portion.

BACKGROUND ART

In a percutaneous administration method of a medicinal ingredient, a skin stratum corneum serves as a barrier against drug permeation, and the medicinal ingredient is not sufficiently permeated only by applying the medicinal ingredient on a skin surface. On the other hand, by inserting the stratum corneum with a very small needle, that is, a microneedle, permeation efficiency of the medicinal ingredient can be drastically improved from the application method. The one integrating a large number of the microneedles on a substrate is a microneedle array. Moreover, a product made easier to be used by adding to the microneedle array an adhesive tape for causing the microneedle array to adhere to the skin or a cover sheet for maintaining an aseptic state until use is called a microneedle patch. The tape, here, refers to the one in which an adhesive is applied on a film, a cloth or paper.

In order to allow the microneedle to hold the medicinal ingredient, two methods are well known. One of them is a method in which a medicinal ingredient is mixed in advance in a microneedle material which is soluble in the body, and the mixture is solidified into a microneedle shape to obtain a medicinal ingredient-containing microneedle. The other is a method in which a previously manufactured microneedle is coated with a solution containing the medicinal ingredient, and it is dried to obtain a microneedle to which the medicinal ingredient adheres. The present application relates to a technique for preparing a coating liquid in which an appropriate medicinal ingredient is dissolved in the latter method.

It should be noted that the solution to coat the microneedle is called a coating liquid, and the one which adhered to the microneedle after the coating and dried and became a part of the microneedle is called a coating material.

To coat a microneedle serving also as an electrode with a medicinal ingredient (Patent Literature 1) and to coat a microneedle made of metal with the medicinal ingredient (Patent Literature 2) have been already reported. A device for quantitatively coating the microneedle with the medicinal ingredient has also been published (Patent Literature 3). However, regarding these trials of coating with the medicinal ingredient, drawbacks that quantitative holding of the medicinal ingredient is difficult in the coating, and that when the microneedle coated with the medicinal ingredient is to be inserted into the skin, the medicinal ingredient is peeled off have been known. In order to cope with them, a trial to make the peeling-off difficult by dissolving a water-soluble polymer similar to the microneedle material in a solution of the medicinal ingredient in advance and by integrating the medicinal ingredient used for the coating and the microneedle has been reported (Patent Literature 4).

In general, a harmless water-soluble or biodegradable polymer which is dissolved and lost in the body is preferable as a microneedle material. A preferable medicinal ingredient solution composition using when a microneedle containing polylactic acid (biodegradable polymer) as a material is coated with the medicinal ingredient is examined (Patent Literature 5), but a coating liquid composition which is optimal for coating a microneedle tip end with the medicinal ingredient has not been examined yet in general.

CITATION LIST

Patent Literature

[Patent Literature 1] National Publication of International Patent Application No. 2002-535100
[Patent Literature 2] National Publication of International Patent Application No. 2004-538048
[Patent Literature 3] National Re-publication of International Patent Application No. WO08/139648
[Patent Literature 4] Japanese Patent Laid-Open No. 2011-224308
[Patent Literature 5] National Re-publication of International Patent Application No. WO10/143689

SUMMARY OF INVENTION

Technical Problem

A problem to be solved by the present invention is to provide a composition of a coating liquid for microneedle which is optimal for coating the microneedle with a medicinal ingredient.

Solution to Problem

A coating liquid for microneedle of the present invention is an aqueous solution containing, as essential components of a base, a water-soluble polysaccharide, a monosaccharide and/or a disaccharide, and a surfactant, characterized in that a ratio of the water-soluble polysaccharide to the base is 5 to 60 mass %.

The coating liquid contains the base and the medicinal ingredient. The base refers to a water-soluble polysaccharide, monosaccharide and/or disaccharide, a surfactant, and a water-soluble polyalcohol in the coating liquid, but supplementary additives excluding the medicinal ingredient are also included in the base other than them. It should be noted that a part of the base can act as the medicinal ingredient in some cases.

A solvent of the coating liquid is basically water, but a mixed solvent containing water-miscible organic solvents such as ethanol, methanol, acetone and the like may be used within a range in which the base or the medicinal ingredient is not precipitated. Therefore, the aqueous solution referred to in this Specification includes the mixed solvent containing organic solvents within a range in which the base or the medicinal ingredient is not precipitated other than the case where the solvent is only water.

In the present invention, the coating liquid is applied on a microneedle tip end and dried, and the obtained medicinal ingredient-applied on tip-end microneedle is percutaneously administrated. At this time, if the coating material is too soft, such a phenomenon occurs that a part or the whole thereof is peeled off in the percutaneous administration and adheres to a stratum corneum. Therefore, the coating material needs to have hardness required for passing through the stratum corneum without peeling-off in the percutaneous administration.

The coating material is constituted by the base and the medicinal ingredient.

The water-soluble polysaccharide in the base forms a robust film and reinforces mechanical strength when being dried. Therefore, the water-soluble polysaccharide is essential for sealing the medicinal ingredient to make a hard coating material.

Moreover, by dissolving the water-soluble polysaccharide in an aqueous solution, viscosity of the aqueous solution is increased, but when the microneedle tip end is soaked in the coating liquid so as to cause the coating liquid to adhere, there is an important relationship between the viscosity of the coating liquid and an adhesion amount. If the viscosity of the coating liquid is appropriate, the microneedle tip end is coated with a large quantity of the coating liquid. If the viscosity of the coating liquid is low, even if the microneedle tip end portion is soaked in the coating liquid, it is not coated with a sufficient amount of the coating liquid in some cases. On the other hand, if the viscosity of the coating liquid is extremely high, adhering property to the microneedle is deteriorated to the contrary, and the coating amount becomes smaller in the end in some cases. A ratio of the water-soluble polysaccharide in the base is preferably 2 to 60 mass % in general.

The water-soluble polysaccharides with various molecular weights are sold in the market. Physical properties of the coating liquid can be optimized by mixing the water-soluble polysaccharides with different molecular weights. It should be noted that the hardness of the microneedle-coating material can be effectively improved by adding water-soluble polymers such as polyvinylpyrrolidone, polyvinylalcohol and the like, for example, to the water-soluble polysaccharide. If the water-soluble polymers such as polyvinylpyrrolidone, polyvinylalcohol and the like are further added, the ratio of the water-soluble polysaccharide and the water-soluble polymer in the base is preferably 2 to 60 mass %.

The monosaccharide and/or disaccharide in the base have an effect of quickening diffusion of the medicinal ingredient in the skin from the coating material. Moreover, it also gives an important contribution to the viscosity of the coating liquid. If the ratio of the monosaccharide and/or disaccharide in the base is low and the ratio of the water-soluble polysaccharide is high, solution of the coating material in the skin requires a long time and thus, emission of the medicinal ingredient in the skin requires a long time in some cases, which is not preferable. Thus, the ratio of the monosaccharide and/or disaccharide in the base is preferably 30 to 95 mass %.

An effect of the surfactant in the base is stabilization of the medicinal ingredient. Protein drugs have poor stability in general. In the present invention, it was found that addition of the surfactant is extremely effective in stabilization of the medicinal ingredient (influenza vaccine antigen). A mechanism of stabilizing the protein drugs in the surfactant is not clear, but it is assumed that the surfactant surrounding the protein in a solution state surrounds and protects the protein even in a state where water is volatized and prevents entanglement or aggregation of proteins by mutual contact. The ratio of the surfactant in the base is preferably 0.05 to 5 mass %. If the ratio is too low, the effect of the surfactant is small, while if the ratio is too high, the coating material after coating becomes soft, the mechanical strength or hardness becomes insufficient, and it can be peeled off easily at insertion.

Liquid polyalcohol in the base is not an essential component, but its role is to soften the coating material by plasticization and to reduce dissolution time of the microneedle. However, if an added amount of the liquid polyalcohol is too large, the coating material becomes too soft, and the coating material is destroyed on the skin surface when it is inserted into the skin, and insertion of the medicinal ingredient into the skin is hindered in some cases. A content rate of the liquid polyalcohol in the base is preferably 10 mass % or less. In relation with the hardness of the coating material, the hardness to compression needed to be 10 N or more from quantitative measurement of various samples.

As the polysaccharide of the coating liquid for microneedle of the present invention, hydroxypropyl cellulose, hyaluronic acid, carboxymethyl cellulose, chondroitin sulfate, algicinic acid or dextran and the like can be suitably used.

As the monosaccharide of the coating liquid for microneedle of the present invention, glucose, and as the disaccharide, sucrose or trehalose can be suitably used.

As the surfactant of the coating liquid for microneedle of the present invention, polysorbate 80, polysorbate 20, polyoxyethylene polyoxypropylene glycol (POP) or a mixture thereof can be suitably used. The polysorbate is an abbreviation of "polyoxyethylene sorbitan mono higher fatty-acid ester".

As the liquid polyalcohol, glycerin, ethylene glycol, propylene glycol, butylene glycol, mannitol, polyethylene glycol with a molecular weight of 500 or less or a mixture thereof can be suitably used.

The coating liquid should have excellent stability of the medicinal ingredient in the coating liquid. If the medicinal ingredient concentration is small, only the efficacy is made smaller, and there is no particular lower limit. All the non-volatile contents (base medicinal ingredient) in the coating liquid are preferably 20 to 40%. If all the non-volatile contents in the coating liquid is 20% or less, it is not suitable for large-quantity coating with the medicinal ingredient, while if it is 40% or more, the viscosity becomes too high, and the coating amount becomes smaller in this case, too.

In this Specification, the medicinal ingredient includes all the compounds that act on the skin or are permeated through the skin and generate some useful actions. The medicinal ingredient does not necessarily have to be water-soluble. It may be a medicinal ingredient dispersed in a suspension state in the coating liquid.

Examples of the medicinal ingredients suitable for the object of the present invention include bioactive peptides and derivatives thereof, nucleic acid, oligonucleotide, various antigenic proteins, bacteria, and virus fragments, for example, and even chemicals made of low molecular weight compounds can be targets of the present invention as long as they exert their features by being made into microneedles. The aforementioned bioactive peptides and derivatives thereof include calcitonin, adrenocorticotrophic hormone, parathyroid hormone (PTH), hPTH (1->34), insulin, growth hormone, growth hormone releasing hormone, bradykinin, substance P, dynorphin, thyroid stimulating hormone, prolactin, interferon, interleukin, G-CSF, glutathione peroxidase, superoxide dismutase, desmopressin, somatomedin, endothelin, and salts thereof. The antigenic proteins can include influenza antigen, HBs surface antigen, HBe antigen and the like.

The viscosity of the coating liquid for microneedle of the present invention is preferably approximately 100 mPa·s to 2500 mPa·s, since there is a concern that an amount of the coating material is reduced if it is too high or too low.

In a coating method, the coating liquid is made to adhere to the microneedle tip end. After the coating, the microneedle is packed and shipped. Therefore, preservation stability of the medicinal ingredient in the coating compound is extremely important.

The coating material needs to be dissolved in the skin after being inserted into the skin. If the dissolution time is too long, it gives a burden to a patient, which is not preferable.

The inventors actually applied the microneedle array coated with the medicament on the microneedle tip end portion to an animal and subjected the corneum of the skin on an applied part to tape-stripping and made measurement and found that a part of the medicament remained on the stratum corneum of the skin. Therefore, even if the microneedle tip end portion can be quantitatively coated with the medicament, when it is actually applied as percutaneous absorbent, the medicament remains on the stratum corneum, and it is likely that the object of quantitative administration of the medicament cannot be achieved, which can be a problem. The microneedle constituting the microneedle array to which the coating liquid for microneedle of the present invention is applied preferably has the following shape.

The microneedle constituting the microneedle array preferably has a needle length of 350 μm or more to 900 μm or less, more preferably of 400 μm or more to 800 μm or less or further preferably of 400 μm or more to 600 μm or less in order to make percutaneous absorption of the drug more reliably.

A diameter of an apex of a needle tip end portion is preferably 20 μm or more to 100 μm or less, or more preferably 30 μm or more to 60 μm or less for easier insertion into the skin and further reduction of remaining of the chemical on the skin.

The individual microneedle has a columnar shape or a conical shape having a circular bottom surface or an elliptic cylindrical shape or an elliptic conical shape having an elliptic bottom surface. When a size of the ellipse is to be expressed, a long diameter is expressed as a diameter, and a short diameter is shorter than the long diameter as long as the ellipse can be formed. The microneedles with these shapes may have a step.

The microneedle array of the present invention has a microneedle-coating material of the present invention at a needle tip end portion. When the tip end of the microneedle is directed upward, a lower end of the coating material is preferably at 200 μm or more from the root of the needle. If the lower end of the coating material is at 200 μm or more from the root of the needle, an upper end may have an arbitrary height according to an amount of the coating material. More preferably, the upper end is the tip end of the microneedle, but coating does not necessarily have to be made up to the tip end. A length of a coated part is typically 100 μm or more to 800 μm or less and preferably 150 μm or more to 600 μm or less.

Advantageous Effect of Invention

The coating liquid for microneedle of the present invention has appropriate viscosity, appropriate adhesion strength, and appropriate solubility in the skin and has good preservation stability of the medicinal ingredient when the microneedle is coated with that. This coating liquid for microneedle is optimal for administration of protein-based drugs.

BRIEF DESCRIPTION OF THE DRAWINGS

FIG. 1 is a microphotograph showing an entire image of a microneedle array used in an example.

DESCRIPTION OF EMBODIMENT

An embodiment of the present invention will be described below on the basis of Examples. However, the present invention is not limited to contents of the Examples.

In the following Examples, a non-water soluble microneedle array (PGA-MN) containing polyglycol acid as a material and a water-soluble microneedle containing hyaluronic acid as a material were used. When the microneedle is coated with the medicinal ingredient, a microneedle tip end was immersed in a coating liquid, picked up, and air-dried for 5 seconds. After the immersion and the air drying were repeated 5 times, it was dried for 12 hours in a dry box (with an atmosphere with humidity of 1 to 2% under a room temperature) to obtain a test sample (dried sample).

Examples

In the Examples shown below, five kinds of measurement were made by using the microneedle array repeatedly coated for 5 times, and results were listed in Table 1 and Table 2. The measurement was made for a coating amount which is an amount of the coating material, adhesion strength which is strength with which the coating material adheres to the microneedle, the solution time in the skin after the coating material adhering to the microneedle array is inserted into the skin, viscosity of the coating liquid, stability of the coated medicinal ingredient, and hardness of the coating material.

Agents and their abbreviations in Table 1 and Table 2 will be described.

As polysaccharides, hydroxypropyl cellulose (HPC-SSL (molecular weight 40000), (HPC-SL (molecular weight 100000), HPC-L (molecular weight 140000), HPC-M (molecular weight 620000), all by Nippon Soda Co., Ltd.)), carboxymethyl cellulose sodium (CMC) (reagent available from Wako Pure Chemical Corporation), or hyaluronic acid (FCH-80, molecular weight 800000), (FCH-200, molecular weight 2 million), (Kikkoman Biochemifa Company)) were used. As the other water-soluble polymers, polyvinylpyrrolidone (PVP) (K-90, Nippon Shokubai CO., Ltd.) was used.

As the monosaccharide/disaccharide, sucrose (suc) or trehalose (tre) was used.

As polyalcohol, glycerin (gly) or propyleneglycol (pg), and mannitol (man) were used, and as a surfactant, polysorbate 80 (p80) or polysorbate 20 (p20) was used.

Moreover, as the medicinal ingredient, an influenza antigen (by BIKEN Co., Ltd.) was used in Examples 1 to 10 and Comparative examples 1 to 5. In Examples 14, 15, 16, and 17, bovine serum albumin (Nacalai Tesque, Inc.) was used.

Units of numeral values of compositions in each agent in Table 1 and Table 2 are mass % in the base. The units of numeral values of the medicinal ingredients are mass parts assuming the base has 100 mass parts. Concentration of the base in the coating liquid was adjusted to 30%. Thus, the full non-volatile content in the coating liquid in Example 1 was 30+20.2×0.3=36.3%, for example.

(Manufacture of Microneedle)

1. Non-Water Soluble Microneedle Array

It was made by an injection molding method using polyglycol acid and used in Examples 1 to 13, 16, and 17 and Comparative examples 1 to 4, 6, and 7. On a circular substrate having a diameter of 10 mm, 480 pieces of the microneedles each having a needle length of 400 μm are provided. Details of the manufacturing method are described in Japanese Patent No. 5852280.

2. Water-Soluble Microneedle Array

It was made by a cast molding method using hyaluronic acid (FCH-80, FCH-200) and carboxylmethyl cellulose and used in Examples 14 and 15 and Comparative example 5. On a circular substrate having a diameter of 10 mm, 280 pieces of the conical microneedles each having a needle length of 800 μm, a diameter of a needle bottom part of 250 μm, and a needle interval of 600 μm are provided.

(Coating of Microneedle Tip End with Base and Medicinal Ingredient)

The microneedle tip end was immersed in the coating liquid and picked up after 0.1 seconds and dried for 5 seconds. The immersion by that operation was repeated 5 times and dried so as to manufacture the microneedle coated with medicinal ingredient on the tip end.

(Evaluation Method and Evaluation Standards)

1. Coating Amount (Total Weight of Medicinal Ingredient and Base)

The microneedle array before and after the immersion was dried, and their masses were compared. The mass before the immersion was subtracted from the mass after so as to acquire a mass (mg) of the coating material. When the mass of the coating material was 1.0 mg or more, it is marked as "double circle", in the case from 0.5 to 1.0 mg, it was marked as "circle", and in the case less than 0.5 mg, it was marked as "cross".

2. Adhesion Strength

The microneedle array after coating/drying was inserted into a Parafilm (thickness of 1 mm) and pulled out, and then, a microphotograph of the microneedle was observed. The adhesion strength of the medicinal ingredient to the microneedle array was examined by that. When the coating material was not peeled off, it was marked as "circle", while if a part of the coating material was peeled off, it was marked as "cross".

3. Solution Time in Skin

The microneedle array after coating/drying 5 times was delivered to a shaved abdominal region of a Wistar rat (male, 4 weeks old) and was taken out after 20 minutes or 40 minutes. The taken-out microneedle patch was observed by a microscope, and a remaining amount of the coating material on the microneedle was checked.

In columns for solution time in Table 1 and Table 2, when the coating material coating the microneedle was fully dissolved within 20 minutes, it was marked as "double circle", when it is fully dissolved within 40 minutes, although it was not fully dissolved within 20 minutes, it was marked as "circle", and when it was not fully dissolved even after 40 minutes, it was marked as "cross". In this test, the microneedle made of hyaluronic acid was used in Examples 14 and 15 and Comparative example 5, and it was observed that not only the coating material but the entire microneedle was dissolved.

4. Viscosity

The viscosity of the coating liquid was measured by using a tuning-fork type vibration viscometer (SV-10, A&D Co., Ltd.). A measurement temperature was 25° C., a sample amount was 10 mL, and measurement time was 15 seconds.

In columns for viscosity in Table 1 and Table 2, when the viscosity was 2500 mPa·s or more, the viscosity was too high and manufacture of the solution and coating were both difficult and thus, it was marked as "cross". When the viscosity was 100 to 2500 mPa·s, coating was easy and a coating amount was also sufficient and thus, it was marked as "circle". When the viscosity was less than 100 mPa·s, the coating was easy but the coating amount was small and thus, it was marked as "two crosses".

5. Medicinal Ingredient Stability Test

By using an influenza vaccine protein as an example of a medicinal ingredient, stability of the medicinal ingredient after coating the microneedle was tested. Micro BCA protein assay kit (Thermo Scientific) was used for assay of the protein. The influenza vaccine protein on the microneedle array was dissolved in water of 0.5 mL, and the influenza vaccine protein mass was measured. The protein mass immediately after the coating and the protein mass after preservation for 3 months at 35° C. were compared. In Examples 14, 15, 16, and 17, evaluation was made for bovine serum albumin by a similar protein assay method.

In columns for stability in Table 1 and Table 2, when the amount after 3-month preservation/amount immediately after manufacture was 0.9 or more, it was marked as "circle", and when this ratio was less than 0.9, it was marked as "cross".

6. Hardness of Coating Material

A coating material sheet having a thickness of 1 mm was manufactured, and a stainless columnar rod having a diameter of 1.5 mm was perpendicularly pressed and compressed by using a small-sized desk tester EZ Test EZSX (Shimadzu Corporation) from above the sheet. A pressing speed was 0.5 mm/min. Inclination of a linear part of an obtained stress-distortion curve was calculated, a compression stress in a pressing distance 0.1 mm was obtained, and hardness (unit: N) of the coating material was quantified.

TABLE 1

Composition of microneedle coating liquid and measurement result

| Example No. | | Base Composition (mass %) | | | | Mass part of medicinal ingredient | Measurement Result | | | | | |
|---|---|---|---|---|---|---|---|---|---|---|---|---|
| | | Polysaccharide, other polymer | Monosaccharide and disaccharide | Poly-alcohol | Sur-factant | | Coating amount | Adhesion strength | Solution time | Viscosity | Stability | Hardness (N) |
| Example | 1 | HPC-L 53.7 | suc 45.0 | gly 0.6 | p80 0.7 | 20.2 | ◎ | ○ | ◎ | ○ | ○ | 53 |
| | 2 | HPC-L 44.2 | suc 55.2 | 0 | p20 0.6 | 23.7 | ○ | ○ | ○ | ○ | ○ | 47 |
| | 3 | HPC-L 17.3 | suc 82.1 | 0 | p80 0.7 | 16.1 | ○ | ○ | ○ | ○ | ○ | 25 |
| | 4 | HPC-SL 59.8 | tre 39.3 | gly 0.5 | p80 0.4 | 16.1 | ◎ | ○ | ◎ | ○ | ○ | 52 |

TABLE 1-continued

Composition of microneedle coating liquid and measurement result

| Example No. | | Base Composition (mass %) | | | | Mass part of medicinal ingredient | Measurement Result | | | | | Hardness (N) |
|---|---|---|---|---|---|---|---|---|---|---|---|---|
| | | Polysaccharide, other polymer | Monosaccharide and disaccharide | Poly-alcohol | Sur-factant | | Coating amount | Adhesion strength | Solution time | Viscosity | Stability | |
| | 5 | HPC-SL 49.8 | tre 49.3 | man 0.5 | p80 0.4 | 16.1 | ○ | ○ | ◎ | ○ | ○ | 45 |
| | 6 | HPC-SSL 44.2 | suc 55.2 | 0 | p20 0.6 | 16.1 | ○ | ○ | ○ | ○ | ○ | 42 |
| | 7 | HPC-SSL 44.2 | tre 55.2 | 0 | p80 0.6 | 20.2 | ○ | ○ | ○ | ○ | ○ | 49 |
| | 8 | HPC-SL 37.3 | suc 62.1 | 0 | p20 0.6 | 23.7 | ○ | ○ | ○ | ○ | ○ | 45 |
| | 9 | HPC-SL 44.6 | tre 55.2 | 0 | p80 0.2 | 20.2 | ○ | ○ | ○ | ○ | ○ | 47 |
| | 10 | HPC-SL 35.0 | suc 62.0 | 0 | p20 3.0 | 23.7 | ○ | ○ | ○ | ○ | ○ | 42 |
| | 11 | HPC-SL 25.0 | tre 74.0 | 0 | p80 1.0 | 0 | ○ | ○ | ○ | ○ | — | 36 |
| | 12 | HPC-SL 20.0 | tre 72.0 | gly 7.0 | p80 1.0 | 0 | ○ | ○ | ◎ | ○ | — | 33 |
| | 13 | HPC-M 2.0 HPC-SL 20.0 | tre 68.0 | gly 9.0 | p80 1.0 | 0 | ○ | ○ | ◎ | ○ | — | 12 |
| | 14 | FCH-80 4.0 CMC 26.0 | suc 65.0 | pg 4.0 | p20 1.0 | 15.0 | ○ | ○ | ○ | ○ | ○ | 65 |
| | 15 | FCH-200 3.0 | tre 92.0 | pg 4.0 | p20 1.0 | 15.0 | ○ | ○ | ○ | ○ | ○ | 22 |
| | 16 | HPC-L 33.0 PVP 21.0 | suc 45.0 | 0.0 | p80 1.0 | 20.0 | ◎ | ○ | ○ | ○ | ○ | 70 |
| | 17 | HPC-SL 25.0 PVP 21.0 | suc 52.0 | 0 | p20 1.0 | 22.0 | ○ | ○ | ○ | ○ | ○ | 65 |

TABLE 2

Composition of microneedle coating liquid and measurement result

| Comparative Example No. | | Base Composition (mass %) | | | | Mass part of medicinal ingredient | Measurement Result | | | | | Hardness (N) |
|---|---|---|---|---|---|---|---|---|---|---|---|---|
| | | Polysaccharide, other polymer | Monosaccharide and disaccharide | Poly-alcohol | Sur-factant | | Coating amount | Adhesion strength | Solution time | Viscosity | Stability | |
| Comparative Example | 1 | HPC-L 72.3 | tre 27.2 | 0 | p80 0.5 | 16.5 | X | ○ | X | X | ○ | 65 |
| | 2 | HPC-L 60.5 | suc 38.0 | gly 0.5 | p80 1.0 | 16.5 | X | ○ | X | X | ○ | 63 |
| | 3 | HPC-L 17.9 | suc 82.1 | 0 | 0 | 23.7 | ○ | ○ | ○ | ○ | X | 29 |
| | 4 | HPC-L 70.5 | tre 28.6 | gly 0.9 | 0 | 16.5 | X | ○ | ○ | X | X | 72 |
| | 5 | FCH-80 10.0 | tre 75.0 | pg 14.0 | p20 1.0 | 15.0 | X | ○ | ○ | X | ○ | 9 |
| | 6 | HPC-L 1.0 | suc 97.0 | gly 1.0 | p20 1.0 | 0 | X | ○ | ○ | XX | — | 15 |
| | 7 | HPC-L 1.0 | suc 78 | gly 20.0 | p20 1.0 | 0 | X | X | ◎ | XX | — | 6 |

7. Corneum Remaining Amount of Medicament Depending on Positions of Coated Part

FITC coated PGA-MN with different (1) needle height, and (2) diameter of needle coated part was subjected to experiments, and FITC remaining amounts on the corneum were examined.

A needle tip end of a microneedle made of PGA (hereinafter, referred to as PGA-MN) was coated with a coating liquid to which FITC which is a fluorescent dye was added and was subjected to rat-applied experiment. After the FITC coated PGA-MN was applied to a rat and removed, stripping was carried out with a tape to remove corneum, and the tape was extracted by a solvent, and fluorescence intensity was measured.

Experiment Method
1. Test Materials

An entire image of the PGA-MN subjected to the rat-applied experiment is illustrated in FIG. 1. In FIG. 1, a PGA-MN substrate has an elliptic shape with a long diameter of 14 mm, a short diameter of 12 mm, and a thickness of 1.0 mm and has a disc-shaped base having a thickness of 1.0 mm and a diameter of 10 mm on top of its upper part. The needle employs a two-stage structure. Dimensions of two types of the PGA-MN with different needle heights subjected to the experiment are illustrated in Table 3.

TABLE 3

Dimension of needle

| | Diameter of Bottom Part (mm) | Height of Bottom Part (mm) | Diameter of Apex of Tip End Portion (mm) | Diameter of Tip End Portion Bottom Part (mm) | Height of Tip End Portion (mm) |
|---|---|---|---|---|---|
| 400 μm PGA-MN | 0.13 | 0.10 | 0.034 | 0.062 | 0.30 |
| 600 μm PGA-MN | 0.12 | 0.30 | 0.032 | 0.060 | 0.30 |

Materials used for coating are as follows:
Hydroxypropyl cellulose (HPC-L) from Nippon Soda Co., Ltd.
Fluorescein-4-isothiocyanate from Dojindo Laboratories 2. Coating Method of PGA-MN Preparation
1) A coating liquid was prepared by mixing FITC dissolved in 0.1 mol/L of NaOH and (HPC-L 50%+SUC 49%+p80 1%) aqueous solution.
2) The PGA-MN tip end was immersed in the coating liquid in a container so that the coating liquid was made to adhere to the needle tip end.
3) It was dried in a desiccator for one night.

3. Application of PGA-MN Preparation to Rat
1) A abdominal region of a Wistar/ST male rat of 8 weeks old was shaved by a shaver, its limbs were fixed with the abdominal region directed upward, and it was anesthetize with somnopentyl.
2) The PGA-MN coated with FITC was pressed and stuck onto the skin on the abdominal region so that the needles were inserted and pressed/fixed by taping.
3) The rat to which the PGA-MN was stuck was placed in a fixator and fixed so that it would not move.
4) The PGA-MN was taken out after 5 minutes or 1 hour.
5) The surface of the applied skin was dried after being left for 10 minutes.

4. Tape Stripping and Extraction/Measurement Method
1) A circular tape with a diameter of 12 mm was stuck to the skin to which the FITC-coated PGA-MN was applied and pressed and then, peeled off. This was repeated 15 times, and the corneum on the skin surface was sampled.
2) 15 pieces of the tape were divided into five each and placed in a 6-well plate and extracted by 0.01 mol/L of NaOH aqueous solution in 1 mL.
3) The FITC-coated PGA-MN before application of the same lot was similarly extracted.
4) The extracted liquid was placed in a 96-well plate, and the fluorescence intensity was measured with a excitation wavelength of 485 nm and a measurement wavelength of 535 nm. For a measuring device, a plate reader, SpectraFluor from Tecan Japan was used.
5) Assuming that the fluorescence intensity of the MN before application is 100, a ratio of the fluorescence intensity of the extracted liquid of 15 pieces of the tape which peeled off the corneum was calculated to obtain a remaining amount on the corneum.

The experiment results can be summarized as follows.

TABLE 4

Summary of rat-applied experiment for FITC-coated PGA-MN

| Condition | Height of Needle (μm) | FITC Coating Amount (ng) | Length of Coated Part (μm) | Diameter of Coated Part (μm) | Remaining Amounts on Corneum (%) |
|---|---|---|---|---|---|
| Removed After 5 min. | 400 | 100 | 200 | 75 | 15.2 |
| | | 200 | 200 | 94 | 50.4 |
| | 600 | 100 | 210 | 65 | 3.3 |
| | | 160 | 210 | 70 | 6.8 |
| Removed After 1 hr. | 400 | 120 | 200 | 75 | 19.0 |
| | | 200 | 210 | 89 | 42.3 |
| | 600 | 100 | 210 | 70 | 9.2 |
| | | 150 | 200 | 70 | 8.8 |

5. Consideration

From the experiment results, it was found that the remaining amount on the corneum after the application was small for the MN with (1) the needle height being high; and (2) the diameter of the coated part being small. By setting the diameter of the coated part in the 600-μm PGA-MN at 70 μm or less, the remaining amount on the corneum was approximately 10% or less, and thus it is considered that practical microneedle preparations can be obtained.

The invention claimed is:

1. A microneedle array having a needle length of 400 μm or more to 800 μm or less and a diameter of an apex of a needle tip end portion of 30 μm or more to 60 μm or less, and having a microneedle-coating material on the needle tip end portion,
   wherein a lower end of the coating material is at 200 μm or more from a root of the needle,
   a hardness of the microneedle-coating material is 10 N or more,
   the microneedle-coating material is obtained by applying a coating liquid for microneedle on a microneedle and drying the coating liquid for microneedle,
   the coating liquid for microneedle comprising an aqueous solution containing, as essential components of a base, a water-soluble polysaccharide, a monosaccharide and/or disaccharide, a surfactant, and a water-soluble polyalcohol,
   wherein, in the base, the water-soluble polysaccharide is 2 to 60 mass %, the monosaccharide and/or the disaccharide is 30 to 95 mass %, the surfactant is 0.05 to 5 mass %, and the water-soluble polyalcohol is 10 mass % or less, the water-soluble polysaccharide is at least one kind of compound selected from the group consisting of hydroxypropyl cellulose, hyaluronic acid, chondroitin sulfate, dextran, and carboxymethyl cellulose, the monosaccharide is glucose, and the disaccharide is sucrose or trehalose, the surfactant is at least one compound selected from the group consisting of polysorbate 80, polysorbate 20, and polyoxyethylene polyoxypropylene glycol, the water-soluble polyalcohol is at least one compound selected from the group consisting of glycerin, ethylene glycol, propylene glycol, butylene glycol, mannitol, and polyethylene glycol with a molecular weight of 500 or less.

2. The microneedle array according to claim 1, wherein the base further comprises polyvinylpyrrolidone.

3. The microneedle array according to claim 2, wherein a total content of the water-soluble polysaccharide and the polyvinylpyrrolidone in the base is 2 to 60 mass %.

4. The microneedle array according to claim 1, further comprising a medicinal ingredient dispersed in a suspension state in the coating liquid, the medicinal ingredient comprising adrenocorticotrophic hormone.

5. The microneedle array according to claim 1, wherein each individual microneedle has an elliptic cylindrical shape or an elliptic conical shape having an elliptic bottom surface.

* * * * *